United States Patent [19]

Thijert et al.

[11] Patent Number: 5,539,106
[45] Date of Patent: Jul. 23, 1996

[54] PROCESS FOR THE PURIFICATION OF A WATER-ε-CAPROLACTAM MIXTURE

[75] Inventors: Marcellinus P. G. Thijert, Sittard; Theodorus A. van der Knaap, Born, both of Netherlands; Johannes F. Haverkort, Martinez, Ga.

[73] Assignee: DSM N.V., Heerlen, Netherlands

[21] Appl. No.: 275,739

[22] Filed: Jul. 19, 1994

[30] Foreign Application Priority Data

Jul. 19, 1993 [BE] Belgium ............................... 09300752

[51] Int. Cl.⁶ ............................................. C07D 201/16
[52] U.S. Cl. .................................................. 540/540
[58] Field of Search ........................................ 540/540

[56] References Cited

U.S. PATENT DOCUMENTS

| 2,786,052 | 3/1957 | Kampschmidt | 540/540 |
| 4,563,308 | 1/1986 | Plantema et al. | 540/540 |
| 5,032,684 | 7/1991 | Neubauer et al. | 540/540 |

FOREIGN PATENT DOCUMENTS

| 138241 | 4/1985 | European Pat. Off. | 540/540 |
| A1411455 | 2/1991 | European Pat. Off. | 540/540 |
| 1332193 | 11/1963 | France | 540/540 |
| 1388442 | 3/1965 | France | 540/540 |
| 3925575 | 9/1991 | Germany | 540/540 |
| 3135958 | 6/1991 | Japan | 540/540 |
| 8303028 | 3/1985 | Netherlands | 540/540 |

*Primary Examiner*—Robert T. Bond
*Attorney, Agent, or Firm*—Cushman Darby & Cushman

[57] ABSTRACT

A process is described for the purification of ε-caprolactam which involves hydrogenation of a water-ε-caprolactam mixture in the presence of a heterogeneous hydrogenation catalyst, wherein the ε-caprolactam-water mixture is contacted with gaseous hydrogen, upon which hydrogen dissolves in the ε-caprolactam-water mixture, and subsequently, this hydrogen-containing mixture is contacted with the hydrogenation catalyst. About 90–100% of the hydrogen is dissolved in the water-ε-caprolactam mixture.

11 Claims, No Drawings

PROCESS FOR THE PURIFICATION OF A WATER-ε-CAPROLACTAM MIXTURE

BACKGROUND OF THE INVENTION

1. Field of the Invention

The invention relates to a process for the purification of ε-caprolactam which involves hydrogenation of a water-ε-caprolactam mixture with hydrogen in the presence of a heterogeneous hydrogenation catalyst.

2. Description of Related Art

To obtain ε-caprolactam of the purity required for polymerization to nylon 6, impure ε-caprolactam, prepared by, for example, Beckmann rearrangement of cyclohexanone oxime, is subjected to a number of purification steps. One of these purification steps is the hydrogenation, as referred to here, of a mixture consisting substantially of water and ε-caprolactam and some unsaturated impurities. Hydrogenation of water-ε-caprolactam mixtures are carried out to hydrogenate these unsaturated compounds present in the impure ε-caprolactam. The presence of these unsaturated compounds are disadvantageous because they can impair the physical-mechanical properties of the nylon-6 made by polymerizing ε-caprolactam. The saturated compounds formed by hydrogenation do not adversely influence these physical-mechanical properties of the nylon-6, and moreover, these compounds are more easily removed in for example a distillation step following the hydrogenation step.

Such a process is described in EP-A-11455, or in U.S. Pat. No. 5,032,684. The process involves the purification, in a three-phase system (gas, liquid, solid), of a 75–95 wt. % aqueous ε-caprolactam mixture in which the water-ε-caprolactam mixture and gaseous hydrogen are passed from the bottom upwards through a fixed bed consisting of a supported palladium or nickel catalyst.

In this known method, the amount of hydrogen fed to the reactor is relatively large, compared with the amount of hydrogen consumed during the reaction. The residual amount of hydrogen is incinerated or recirculated to the hydrogenation reaction. In the latter case, the hydrogen is passed through a compressor to ensure that it has the correct pressure when it is returned to the reactor. A drawback of this process is that large amounts of hydrogen have to be processed which will result in more safety measures, because of the nature of hydrogen. A further drawback of the method is that the system requires a relatively large compressor to keep a large amount of hydrogen in circulation. When the residual amount of hydrogen is incinerated, economics prove to be unattractive because the burning value of hydrogen is less than the hydrogen cost price.

SUMMARY OF THE INVENTION

Objects for the present invention include, but are not limited to, providing a more efficient and more safe process for the purification of ε-caprolactam.

This is achieved by: (i) contacting a water-ε-caprolactam mixture with hydrogen, whereby the hydrogen dissolves in the water-ε-caprolactam mixture to yield a water-ε-caprolactam-hydrogen mixture, and (ii) contacting the water-ε-caprolactam-hydrogen mixture with a hydrogenation catalyst, wherein about 90–100% of the hydrogen during contacting is dissolved in the water-ε-caprolactam mixture. About 90–100% of the hydrogen present during hydrogenation has been dissolved in the water-ε-caprolactam mixture. Preferably, about 98–100% of the hydrogen has been dissolved in the water-ε-caprolactam mixture. When, for example, 98% of the hydrogen is dissolved in the mixture, the remaining 2% of the hydrogen is in the gaseous phase.

In the process disclosed herein, a mixture comprising substantially water, ε-caprolactam, and unsaturated impurities can be purified to yield ε-caprolactam of the same purity as the ε-caprolactam purified by the process disclosed in EP-A-411,455, but without a large amount of unreacted hydrogen remaining after hydrogenation. This allows for use of simpler reactor equipment. Furthermore, there is no need to install equipment for recirculating unreacted hydrogen or equipment for incinerating hydrogen.

In the process disclosed herein, the residence time of the liquid in the hydrogenation reactor can be shortened substantially compared to the process disclosed in EP-A-411455. A short residence time is advantageous because either a smaller reactor volume can be used while the reactor load remains the same, or a higher reactor load can be used while using the same reactor volume.

As described hereinafter, further advantages can be found in the method to activate the catalyst for hydrogenation.

DETAILED DESCRIPTION OF THE PRESENT INVENTION

According to the process of the invention disclosed herein, very little hydrogen is present in gaseous form in the hydrogenation reactor. In contrast to the conventional thinking, a quantity of hydrogen that can dissolve in the reaction mixture under the reaction conditions is sufficient to purify the ε-caprolactam. Hydrogen is a difficult gas to compress, due to its small molecular size, and use of less hydrogen also results in improved safety.

When the ε-caprolactam-water mixture is contacted with the gaseous hydrogen, the mixture will become completely or partially saturated with hydrogen.

The degree to which the reaction mixture generally is saturated with hydrogen is between about 50–100%. Preferably, the degree of saturation of the reaction mixture is between about 80–100%. The amount of hydrogen in the reaction mixture will depend on temperature, pressure and contact time of the hydrogen and the mixture when dissolving the gaseous hydrogen. The degree of saturation is the percentage of the maximum amount of hydrogen which can dissolve in the mixture at a certain temperature and pressure. By adding more than the maximum amount of hydrogen, a gaseous phase will be present. It has been found that the solubility of hydrogen in the water-ε-caprolactam mixture is almost comparable with the solubility of hydrogen in pure water for the mixtures which can be treated with the process according to the invention (thus irrespective of the ε-caprolactam concentration).

The ε-caprolactam weight percentage in the water-ε-caprolactam mixture (excluding hydrogen) may be between about 10 and 95 wt. %. A low ε-caprolactam content is advantageous as it allows for dissolution of a larger amount of hydrogen. However, a very low ε-caprolactam content is not advantageous, for in that case, a large quantity of inert water circulates and evaporates. The ε-caprolactam content will therefore preferably be higher than about 30 wt. %. Preferably, the ε-caprolactam content is lower than about 50 wt. %, and most preferably, it is below about 40 wt. %.

The heterogeneous catalyst can be contacted with the hydrogen-containing reaction mixture in various ways. Hydrogenation may for instance take place in a stirred tank reactor in which the catalyst particles are suspended in the mixture to be purified (slurry phase process). A drawback of the slurry phase process is that the catalyst particles and the purified mixture must be separated in an additional process step after the hydrogenation reaction. Such a separation step, for instance by means of filtration, is cumbersome. Therefore, the hydrogenation is more preferably effected in a fixed-bed reactor with the catalyst being fixed in the reactor, so that the additional step for separation of the catalyst and reaction mixture can be dispensed with.

The hydrogenation temperature is generally between about 20° and 160° C. As a rule, a not too low temperature will be chosen, for at a low temperature the reaction time can be longer. The temperature is, as a rule, not too high because high temperatures can have a negative influence on the ε-caprolactam quality. The temperature therefore preferably is between about 70° and 130° C. and most preferably, between about 80° and 100° C.

The hydrogenation pressure may be between about 0.1 and 15 MPa. High pressures are advantageous as they allow dissolution of a larger quantity of hydrogen in the water-ε-caprolactam mixture. Since the impurity content is normally not so high as to necessitate a large quantity of hydrogen, an excessively high pressure is not needed. Very high pressures further have the drawback that expensive process equipment is needed. As a rule, therefore, the pressure is between about 0.3 and 5 MPa.

The process according to the invention can be performed batchwise. Preferably, the process is performed as a continuous process.

The hydrogenation residence time or contact time depends on the method that is chosen for contacting the heterogeneous catalyst with the hydrogen-containing water-ε-caprolactam mixture. If a reactor is chosen in which the catalyst is fixed in the reactor (fixed-bed reactor), the residence time in a continuous process is generally more than about 10 seconds, and in particular, more than about 30 seconds. In general, the residence time is less than about 10 minutes, and in particular, less than about 7 minutes.

The amount of hydrogen used per amount of ε-caprolactam to be purified will depend on the temperature, pressure, degree of saturation and solubility of hydrogen, and the degree of impurities to be hydrogenated.

If the process is applied without recycling of non-converted hydrogen, the hydrogen volume quantity per weight quantity of caprolactam to be purified (excluding water) as a rule is between about 0.001 and 2 $Nm^3$/tonne lactam (between about $5\times10^{-6}$ and $1.0\times10^{-2}$ mol $H_2$ per mol ε-caprolactam) and preferably, between about 0.1 and 1 $Nm^3$/tonne lactam ($5\times10^{-4}$ and $5\times10^{-3}$ mol $H_2$ per mol ε-caprolactam).

Dissolution of the hydrogen in the water-ε-caprolactam mixture can be effected by any process that is known to one skilled in the art. Preferably, the mixture is contacted with hydrogen in a mixer in which a constant hydrogen pressure is maintained. Intensive contact between the hydrogen and the mixture will ensure that the hydrogen dissolves in the mixture. Such a process is preferably carried out continuously. The hydrogen-containing mixture is subsequently contacted with the hydrogenation catalyst in, for example, a separate reactor.

As a rule, the pressure and the temperature during hydrogen dissolution in the water-ε-caprolactam mixture are virtually the same as the pressure and temperature that is maintained in the hydrogenation reactor. Depending on specific conditions, for instance in the case of heat recovery, there may be a somewhat larger difference between the pressure and temperature at which hydrogen dissolution takes place and the hydrogenation pressure and temperature.

The hydrogenation catalysts may be any known heterogeneous hydrogenation catalyst. Examples of such catalysts are ruthenium on aluminum oxide, rhodium on aluminum oxide, platinum on carbon, palladium on carbon, Raney nickel, nickel on silica and nickel on aluminum oxide. Preferably, use is made of nickel-containing catalyst.

Suitable nickel catalysts, as a rule, have a nickel content between about 5 and 80 wt. %, relative to the metal and the support. Besides nickel, the catalyst may contain some activators such as Zr, Mn, Cu or Cr. The activator content is generally between about 1 and 20 wt. %.

If palladium-containing heterogeneous catalysts are used, the palladium content will generally be between about 0.01 and 10 wt. %.

If a fixed-bed reactor is used, catalysts are employed in which an active metal is on the external surface of a support. Such catalysts can be prepared using the method in which a pre-formed support (for instance pellets, spheres or ribbons) is contacted with an aqueous solution of a metal salt, for example the metal nitrate, dried, and subsequently calcined.

The size of the pre-formed support that is chosen will be as small as possible without the pressure drop across the fixed bed becoming unacceptable. For example, the average particle diameter of pellets is usually between about 1 and 5 mm In cases when freshly prepared catalyst is used, the catalyst can be activated in order to reduce the metal oxides to catalytically active free metal.

Catalyst activation can be effected in any known manner. For example hydrogen can be used to reduce the metal oxides. In Example 3 of EP-A-411455, for example, the catalyst is activated by passing gaseous hydrogen over the catalyst for 8 hours while increasing the temperature stepwise from 80° to 200° C. This known process for activating the hydrogenation catalyst is, however, disadvantageous because large quantities of valuable hydrogen are consumed by the process. It has now been found that activation can be carried out in a temperature range of about 70°–100° C. if the catalyst to be activated is contacted with water in which hydrogen is dissolved. The activation pressure may be between about 0.1 and 10 MPa. In comparison with the activation as described in EP-A-411455, the above-mentioned activation is advantageous because: (1) catalyst activation is carried out at a lower (maximum) temperature, (2) catalyst activation is carried out in situ so that no extra facilities are needed to pass gaseous hydrogen to the catalyst bed especially for the activation, and (3) no excessive usage of hydrogen is necessary.

In order to prepare the aqueous solution of hydrogen needed for catalyst activation, hydrogen can be dissolved in water in the same way as previously described for dissolution of hydrogen in the mixture of water, ε-caprolactam, and unsaturated impurities. Concerning the catalyst activation process, the reaction conditions used to dissolve hydrogen in water are virtually the same as the reaction conditions, such as temperature and pressure, used to activate the catalyst.

Activation of the catalyst can also be carried out using the previously described mixture of water, ε-caprolactam, hydrogen, and unsaturated impurities. This mixture can be contacted with the hydrogenation catalyst in the same manner as in the purification described above at a temperature between about 70°–100° C. The advantage of using this mixture directly is that catalyst activation can be carried out, in situ, when the purification is started without any adaption of the process operation. Under normal operating conditions, applying a hydrogen containing water-ε-caprolactam mixture as described above, about 12 to 48 hours are sufficient to activate the catalyst to a level at which high-purity ε-caprolactam can be obtained.

The ε-caprolactam to be purified can be prepared by the Beckmann rearrangement in oleum, as described in DE-A-2508247, or other preparation processes, such as for instance the rearrangement reaction in the presence of an acid ion exchanger as described in GB-A-1342550. Caprolactam obtained by depolymerization of nylon 6, as described in U.S. Pat. No. 5,169,870, can also be purified advantageously using the process according to the invention.

In practice, the purity of ε-caprolactam obtained by purification of a mixture of water-ε-caprolactam by evaporation and distillation (as is disclosed in U.S. Pat. No. 4,563,308) is expressed by the permanganate absorption number (PAN). The PAN is determined in accordance with ISO 8660. ε-caprolactam obtained from an unpurified mixture of water, ε-caprolactam and unsaturated impurities generally has a PAN ranging from about 4 to 6. The PAN of ε-caprolactam obtained from a water-ε-caprolactam mixture that has been purified according to the invention disclosed herein is generally lower than about 4 and generally higher than about 1. Preferably, the PAN is lower than 3.

Another way of expressing the purity of the ε-caprolactam eventually obtained is by means of the PM number (permanganate number). Like PAN, the PM number is a measure of the oxidizability. A higher PM number means that a smaller amount of oxidizable impurities is present. Yet another way of expressing the purity is by means of the amount of unsaturated compounds (in ppm).

The 'permanganate number' (=PM number) is defined as the number of seconds elapsing after the addition of 1.00 ml of potassium permanganate 0.0020 Mol/l to 100 ml of caprolactam solution (3.00 g/100 ml) at 293 K. (=20° C.) until the moment at which the color of this solution becomes equal to the color of a standard solution. The standard solution consists of 3,000 mg of cobalt nitrate $(Co(NO_3)_2 \cdot 6 H_2O)$ and 12 mg of potassium dichromate in 1 l water. The PN number may only be used for comparison purposes of the Experiments and Examples as described below.

A process for the purification of ε-caprolactam which involves hydrogenation of a water-ε-caprolactam mixture is described in Belgium Patent Application Serial No. 09300752, filed Jul. 19, 1993, for which the full text is incorporated herein by reference.

The invention will be elucidated by means of the following non-limiting examples.

EXAMPLES I–III

The aqueous caprolactam in these examples was obtained by Beckmann rearrangement of cyclohexanone oxime in oleum and neutralization with ammonia, benzene extraction followed by a reextraction with water. The mixture after neutralization was introduced into a 1.0 l stirred reactor together with benzene (3 g mixture/1.5 g benzene). The resulting mixture was stirred for 15 minutes and subsequently two phases, a "water phase" and a "benzene phase" formed, which were separated by phase separation.

The water phase was again introduced into the reaction together with fresh benzene (5.0 benzene/10.0 g waterphase). The mixture was again stirred for 15 minutes and subsequently separated into two phases. This extraction step with benzene was repeated two additional times. The resulting "four benzene phases" were mixed with fresh water (25 g/100 g benzene phase). This mixture was stirred for 15 minutes and subsequently separated into two phases.

This water extraction was repeated two additional times. The resulting water phases from the benzene extraction and the water phases obtained from the water extraction were mixed together. This yield a 35 wt. % caprolactam solution in water. A process according to the invention was used to treat this mixture further by saturating the solution with hydrogen in step a) and passing the solution over a hydrogenation catalyst in step b).

a) In a continuously operated, stirred tank (diameter 100 mm, filling level 100 mm and provided with a heating jacket) the 35 wt. % caprolactam solution in water was fully pre-saturated in a mixer in which a constant hydrogen pressure of 0.6 MPa was maintained with a pH 7 and the temperature stated in Table 1.

b) Through a vertical tubular reactor (diameter 34 mm, filling level 27 mm, heating jacket) filled with 25 ml (20 grams) nickel catalyst (ca. 50 wt. % nickel (oxide) on alumina/silica, diameter 3 mm, length 8 mm) a continuous flow was established of the hydrogen-saturated caprolactam solution. The flow passed through the catalyst bed from the bottom upwards at the same temperature as in Table 1 and at 6 bar and pH 7 (for flow rates see Table 1). In situ catalyst activation took place.

After 12 hours, the first sample was taken. The sample was further processed by means of evaporation and distillation as described in Example of U.S. Pat. No. 4,563,308, after which the PAN and the PM number as well as the total quantity of compounds to be hydrogenated were determined. The results are given in Tables 1 and 2. Hydrogenation was continued for 10 days. The purification of the final product did not deviate significantly from the results listed in Table 2. This proved that catalyst activation had been completed after about 12 hours.

TABLE 1

| Example | Temp. (°C.) | Liquid flow rate (g/h) 1) | H2 consumption (nl/h) 2) | Resisdence time (sec.) |
|---------|-------------|---------------------------|--------------------------|------------------------|
| I       | 90          | 250                       | 0.03                     | 145                    |
| II      | 85          | 500                       | 0.03                     | 75                     |
| III     | 100         | 250                       | 0.022                    | 145                    |

1) g/h = grams of water/ε-caprolactam/hydrogen mixture per hour
2) nl/h = normal liter of hydrogen consumed in the stirred tank per hour The water-ε-caprolactam mixture with the dissolved hydrogen was in all the Examples I–III a substantially homogeneous mixture (substantially no gas phase present).

The amount of unsaturated compounds in the caprolactam solution fed to and discharged from the hydrogenation was determined; the results are presented in Table 2.

TABLE 2

| Ex. | PAN 1) | PM (sec.) 2) | ppm in feed | ppm in discharge |
|-----|--------|--------------|-------------|------------------|
| I   | 1.8    | 39,000       | 10          | <1               |
| II  | 2.1    | 35,000       | 5           | <1               |
| III | 1.9    | 45,000       | 10          | <1               |

1) measured according to ISO 8660

TABLE 2-continued

| Ex. | PAN 1) | PM (sec.) 2) | ppm in feed | ppm in discharge |
|---|---|---|---|---|

2) PM number. A higher number indicates that a lower amount of oxidizable impurities is present.

Comparative Experiment A

Without further purification (hydrogenation), the 35 wt % caprolactam mixture in water of Example I was evaporated and distilled in the same way as in Example I. The caprolactam proved to have a PAN of 5 and a PM of 12,000 sec.

Comparative Experiments B–E

The 35 wt. % aqueous caprolactam solution used in these experiments is the same as that used in Example I (after extraction). In this series of experiments, use was made of a bubble column according to EP-A-411455. Contrary to Examples I–III, a large quantity of gaseous hydrogen was present during hydrogenation.

a) A vertical tubular reactor (diameter 34 mm, filling level 27 cm, jacket hearing) was filled with 250 ml already activated (160) nickel catalyst (ca. 50 wt. % nickel/ nickel oxide on alumina, for diameter (d) see Table 3, length 5 to 8 mm). Hydrogenation was effected by pumping gaseous hydrogen (25 nl/h) and the caprolactam solution in water (35 wt. % caprolactam) for 90 minutes through the bed from the bottom upwards, this taking place at 90° C., 0.6 MPa and pH 7.

The other conditions are listed in Table 3. The concentration of unsaturated compounds was determined both in the feed and in the discharge flow.

TABLE 3

| Exp. | Temp. (°C.) | Residence time (min.) | Liquid flow rate (g/h) | $H_2$ flow rate (nl/h) | $d_{cat}$ (mm) |
|---|---|---|---|---|---|
| B | 90 | 18 | 250 | 25 | 1.6 |
| C | 90 | 18 | 250 | 25 | 3.2 |
| D | 90 | 9 | 500 | 25 | 1.6 |
| E | 90 | 9 | 500 | 25 | 3.2 |

Upgrading of the caprolactam solution in water by evaporation and distillation (as in Example I) resulted in the final product quality as indicated in Table 4.

TABLE 4

| Exp. | PAN | PM | ppm in feed | ppm in discharge |
|---|---|---|---|---|
| B | 1.9 | 35,000 | 11 | <1 |
| C | 2.3 | 35,000 | 11 | <1 |
| D | 2.3 | 37,000 | 11 | <1 |
| E | 3.0 | 27,000 | 11 | 2 |

The results show that use of a packed bubble column at the same load and a longer residence time leads to comparable purities, with hydrogen consumption being many times higher.

While the invention has been described in detail and with reference to specific embodiments thereof, it will be apparent to those of ordinary skill in the art that various changes and modifications can be made therein without departing from the spirit and scope thereof.

What is claimed is:

1. A process for the purification of $\epsilon$-caprolactam which consists essentially of (i) contacting a water-$\epsilon$-caprolactam mixture with hydrogen to obtain a water-$\epsilon$-caprolactam-hydrogen mixture, and (ii) contacting said water-$\epsilon$-caprolactam-hydrogen mixture with a hydrogenation catalyst, wherein about 90–100% of the hydrogen present during said contacting (ii) is dissolved in said water-$\epsilon$-caprolactam-hydrogen mixture.

2. A process according to claim 1, wherein at least 98% of the hydrogen present during said contacting (ii) is dissolved in said water-$\epsilon$-caprolactam-hydrogen mixture.

3. A process according to claim 1, wherein the amount of said hydrogen relative to the amount of said $\epsilon$-caprolactam is between about $5\times10^{-4}$ and $5\times10^{-3}$ mol hydrogen per mol $\epsilon$-caprolactam.

4. A process according to claim 1, wherein the concentration of $\epsilon$-caprolactam is between about 10 and 40 wt. %.

5. A process according to claim 1, wherein the temperature during said process is between about 70° C. and about 130° C.

6. A process according to claim 5, wherein the temperature is between about 80° C. and 100° C.

7. A process according to claim 1, wherein said process is carried out in a fixed bed.

8. A process according to claim 7, wherein said process is carried out continuously with a residence time between about 10 seconds and 10 minutes.

9. A process according to claim 1, wherein said hydrogenation catalyst is activated in situ by contacting said water-$\epsilon$-caprolactam-water mixture with said hydrogenation catalyst at a temperature between about 70° C. and 100° C.

10. A process for the purification of $\epsilon$-caprolactam which consists of (i) preparing a mixture consisting essentially of water, $\epsilon$-caprolactam and hydrogen by contacting a water-$\epsilon$-caprolactam mixture with hydrogen, and (ii) contacting said water-$\epsilon$-caprolactam-hydrogen mixture with a hydrogenation catalyst, wherein during said contacting (ii) is conducted in the substantial absence of gaseous hydrogen and wherein about 90–100% of the hydrogen present during said contacting (ii) is dissolved in said water-$\epsilon$-caprolactam-hydrogen mixture.

11. A process for the purification of $\epsilon$-caprolactam which consists of (i) contacting a water-$\epsilon$-caprolactam mixture with hydrogen to obtain a water$\epsilon$-caprolactam-hydrogen mixture, and (ii) contacting said water$\epsilon$-caprolactam-hydrogen mixture with a hydrogenation catalyst, wherein about 90–100% of the hydrogen present during said contacting (ii) is dissolved in said water$\epsilon$-caprolactam-hydrogen mixture.

\* \* \* \* \*